(12) United States Patent
Hondori et al.

(10) Patent No.: US 10,874,224 B2
(45) Date of Patent: Dec. 29, 2020

(54) SURGICAL ROBOTIC SYSTEM HAVING ANTHROPOMETRY-BASED USER CONSOLE

(71) Applicant: Verb Surgical Inc., Mountain View, CA (US)

(72) Inventors: Hossein Mousavi Hondori, Mountain View, CA (US); Joan Savall, Palo Alto, CA (US); Hamid Reza Sani, Belmont, CA (US); Brent Michael Nobles, Palo Alto, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 173 days.

(21) Appl. No.: 16/035,549

(22) Filed: Jul. 13, 2018

(65) Prior Publication Data
US 2020/0015598 A1 Jan. 16, 2020

(51) Int. Cl.
| | | |
|---|---|---|
| *A47C 31/12* | (2006.01) | |
| *G06N 20/00* | (2019.01) | |
| *A61B 34/35* | (2016.01) | |
| *B25J 9/16* | (2006.01) | |
| *B25J 13/04* | (2006.01) | |

(Continued)

(52) U.S. Cl.
CPC .............. *A47C 31/126* (2013.01); *A47C 1/02* (2013.01); *A47C 3/20* (2013.01); *A47C 7/56* (2013.01); *A47C 7/723* (2018.08); *A61B 34/25* (2016.02); *A61B 34/35* (2016.02); *B25J 9/1689* (2013.01); *B25J 13/04* (2013.01); *G06N 20/00* (2019.01); *G16H 20/40* (2018.01); *A61B 5/1077* (2013.01);
(Continued)

(58) Field of Classification Search
None
See application file for complete search history.

(56) References Cited

U.S. PATENT DOCUMENTS

| | | | | |
|---|---|---|---|---|
| 4,452,449 A | * | 6/1984 | Propst | A47C 3/026 482/41 |
| 6,078,854 A | * | 6/2000 | Breed | B60N 2/002 701/49 |

(Continued)

FOREIGN PATENT DOCUMENTS

WO WO2017124170 A1 7/2017

OTHER PUBLICATIONS

International Search Report and Written Opinion dated Jun. 24, 2019 for related PCT Appln. No. PCT/US2018/043173 21 Pages.

*Primary Examiner* — Bickey Dhakal
(74) *Attorney, Agent, or Firm* — Womble Bond Dickinson (US) LLP

(57) ABSTRACT

Surgical robotic systems including a user console for controlling a robotic arm or a surgical robotic tool are described. The user console includes components designed to automatically adapt to anthropometric characteristics of a user. A processor of the surgical robotic system is configured to receive anthropometric inputs corresponding to the anthropometric characteristics and to generate an initial console configuration of the user console based on the inputs using a machine learning model. Actuators automatically adjust a seat, a display, or one or more pedals of the user console to the initial console configuration. The initial console configuration establishes a comfortable relative position between the user and the console components. Other embodiments are described and claimed.

20 Claims, 7 Drawing Sheets

(51) Int. Cl.
*A47C 3/20* (2006.01)
*A47C 7/56* (2006.01)
*A47C 7/72* (2006.01)
*A47C 1/02* (2006.01)
*G16H 20/40* (2018.01)
*A61B 34/00* (2016.01)
*B25J 13/06* (2006.01)
*A61B 17/29* (2006.01)
*A61B 5/107* (2006.01)

(52) U.S. Cl.
CPC ......... *A61B 17/29* (2013.01); *A61B 2034/258* (2016.02); *B25J 13/065* (2013.01)

(56) References Cited

U.S. PATENT DOCUMENTS

| | | | |
|---|---|---|---|
| 9,022,468 B2* | 5/2015 | Shalaby | A47C 31/126 |
| | | | 297/217.2 |
| 9,921,726 B1* | 3/2018 | Sculley | H04L 67/12 |
| 2010/0225209 A1 | 9/2010 | Goldberg | |
| 2012/0053794 A1 | 3/2012 | Alcazar et al. | |
| 2015/0366350 A1* | 12/2015 | Di Censo | A47C 1/00 |
| | | | 700/275 |
| 2016/0280161 A1 | 9/2016 | Lippman et al. | |
| 2017/0101032 A1 | 4/2017 | Sugioka et al. | |
| 2017/0305437 A1 | 10/2017 | Onorato et al. | |
| 2018/0078319 A1 | 3/2018 | Nobles | |
| 2018/0092706 A1 | 4/2018 | Anderson | |
| 2018/0332966 A1* | 11/2018 | Lohken | A47C 31/126 |

* cited by examiner

SURGICAL ROBOTIC SYSTEM HAVING ANTHROPOMETRY-BASED USER CONSOLE

BACKGROUND

Field

Embodiments related to surgical robotic systems are disclosed. More particularly, embodiments related to automatically adjusting user console configurations in surgical robotic systems are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command robotically-assisted tools and at least one camera located at an operating table. The surgeon may use a user console located in the operating room (or in a different city) to command a robot to manipulate the surgical tool and the camera. For example, the surgeon may hold in her hand a user input device such as a joystick or a computer mouse that she manipulates to generate control commands that cause motion of the surgical robotic system components, e.g., the surgical tool or the camera. The robot uses the surgical tools to perform surgery, with the visualization aid provided by the camera.

The surgeon may be seated at the user console of the surgical robotic system for extended periods of time during surgery. The extended surgical sessions can induce fatigue and/or physical discomfort for the surgeon. Accordingly, surgical robotic systems may have seats that the surgeon can manually adjust to a comfortable position.

SUMMARY

Existing user consoles of surgical robotic systems allow a surgeon to manually adjust a seat to a variety of positions. The surgeon can raise, tilt, or translate the seat to a preferred position. The preferred position can be a position that the surgeon finds most comfortable, which may improve surgical performance, especially during lengthy operations. Manual adjustability of the seat, however, may introduce several unnoticed and/or undesirable effects. The surgeon may waste time or spend too long adjusting the seat because the seat adjustability may have many degrees of freedom for requiring adjustment. The surgeon may fail to find an optimal configuration, i.e., a "sweet spot," because although the surgeon may feel comfortable after initially adjusting the seat position, the seat position may actually be a temporarily optimal position. That is, the seat position may induce more user fatigue over long periods of time than would a different, long-term, optimal position would. The difference between the temporarily optimal position and the long-term optimal position, however, may be unnoticeable to the surgeon at the time of adjustment.

Surgical robotic systems including a user console having a seat, a display, and/or one or more pedals designed to automatically adapt to anthropometric characteristics of a user are described. It has been determined that there are correlations between anthropometric characteristics of individuals and the optimal setup of the user console for those individuals, including user/seat poses, distances and angles of the display or pedals, and positions of the display or pedals relative to the user/seat poses. The user console includes a processor configured to generate a recommended/initial configuration based on anthropometric inputs corresponding to physical attributes of the user. The processor can use a machine learning (ML) model to predict optimal positions and poses of the seat, display, or pedals based on the identified physical attributes. The output configuration may be used by the processor to drive one more console actuators to adjust one or more of the seat, the display, or the pedals to the recommended initial configuration. The initial configuration is a predicted optimal settings of the user console for long-term use.

In an embodiment, one or more actuators of the user console can adjust the user console to the recommended/initial configuration. The initial configuration establishes a comfortable relative position between the user and one or more components of the surgical robotic system. For example, the initial console configuration can position a face of the user relative to the display in a manner that facilitates correct and comfortable viewing of the display. By way of example, a viewing distance or a viewing angle of the user can be adjusted by movement of the seat to the initial console configuration.

In an embodiment, the ML model receives a limited number of inputs corresponding to physical attributes of the user to derive the recommended console configuration. For example, the user may enter information that is readily known, such as a height, shoe size, or gender of the user. The ML model may include multi-stage ML models to generate the output configurations. For example, a first ML model can correlate the limited input data to a broader set of physical attribute data including information that is not readily known, such as the user's arm length or lower leg length. A second ML model can correlate the broader set of data output by the first ML model to the console configurations. Accordingly, surgical robotic system can recommend console settings using the ML models and automatically set up the console components to a recommended initial configuration based on entry of only a few well-known parameters.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
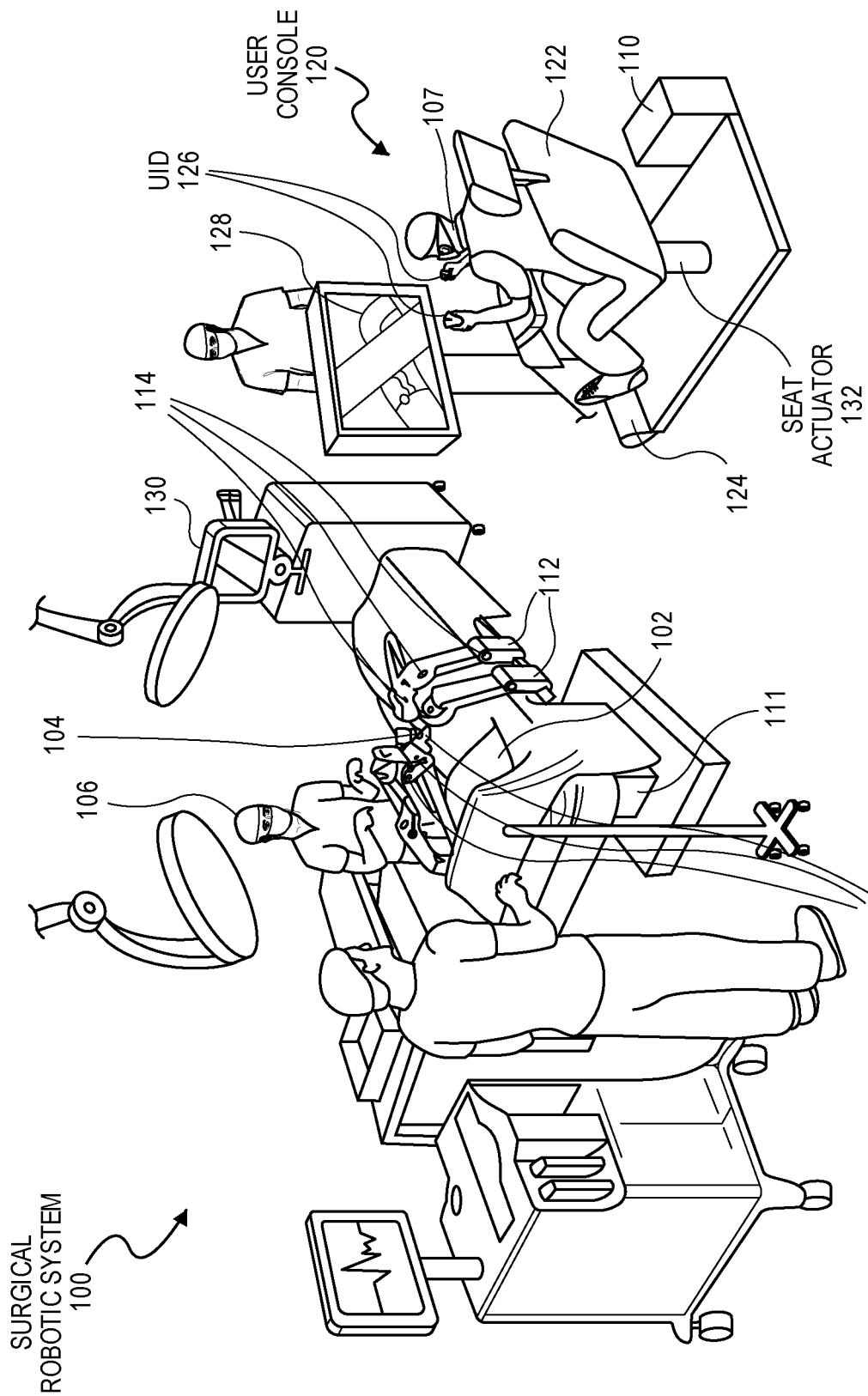
FIG. 1 is a pictorial view of a surgical robotic system in an operating arena, in accordance with an embodiment.

Embodiments describe a surgical robotic system having a user console for controlling a robot. The user console includes adjustable components, such as a seat, a display, and/or one or more pedals which are automatically adjustable to an optimal position for a current user. The user console having adjustable components may be incorporated in other systems, such as aircraft systems or automobile systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "forward" may indicate a first direction away from a reference point, e.g., in front of a seat. Similarly, "backward" may indicate a location in a second direction opposite to the first direction, e.g., behind the seat. Such terms are provided to establish relative frames of reference, however, and are not intended to limit the use or orientation of a surgical robotic system to a specific configuration described in the various embodiments below.

It has been discovered that there are correlations between a user-preferred configuration of a user console and physical attributes of the user. For example, a seating configuration, which may be defined by a seat lift, a seat recline, or a seat translation parameter, or a display configuration, which may be defined by a display lift or a display tilt parameter, correlates with a height, arm length, leg length, shoe size, etc., of the user. In an aspect, a surgical robotic system predicts an optimal initial console configuration of a seat, a display, or another system component such as one or more pedals, for a user based on the anthropometric characteristics of the user. The surgical robotic system includes a processor configured to receive anthropometric inputs (or parameters) corresponding to the anthropometric characteristics and to recommend initial (or optimal) console configurations using a machine learning (ML) model. For example, the ML model may include at least two regression ML models arranged in a serial order. Actuators of the console system (e.g., seat actuators), can adjust respective components based on the recommended console configuration. The initial console configuration may be a predicted preferred position of the user, and can establish a relative viewing position and angle between the user and the display of the user console. By optimizing the initial console configuration, fatigue and/or discomfort of the user may be reduced during long surgeries. Greater comfort can lead to better surgical performance and surgical outcomes.

Referring to FIG. 1, a pictorial view of a surgical robotic system in an operating arena is shown in accordance with an embodiment. A surgical robotic system 100 comprises a user console 120, a control tower 130, and one or more robotic arms 112 located at a surgical platform 111, e.g., mounted on a table, a bed, etc. Surgical robotic system 100 can incorporate any number of devices, tools, or accessories used to perform surgery on a patient 102. For example, surgical robotic system 100 may include one or more surgical tools 104 used to perform surgery. Surgical tools 104 can be end effectors attached to distal ends of robotic arms 112 for executing a surgical procedure.

Each surgical tool 104 can be manipulated manually and/or robotically during the surgery. For example, surgical tool 104 may be a tool used to enter, view, or manipulate an internal anatomy of patient 102. In an embodiment, surgical tool 104 is a grasper used to grasp tissue of patient 102. Surgical tool 104 can be manually handled by a bedside operator 106, or robotically controlled by movement of robotic arms 112. Robotic arms 112 are shown as a table-mounted system, but in other configurations, robotic arms 112 may be mounted in a cart, ceiling or side wall, or other suitable support surface within the operating arena.

Generally, a user 107, such as a surgeon or other operator, may use user console 120 to remotely manipulate robotic arms 112 and/or surgical tools 104, e.g., by tele-operation. User console 120 may be located in the same operating arena or room as robotic arms 112 as shown in FIG. 1. In other environments, user console 120 may be located in an adjacent or nearby room, or tele-operated from a remote location in a different building, city, or country. User console 120 may comprise a seat 122, one or more foot-operated control pedals 124, one or more handheld user interface devices (UIDs) 126, and at least one user display 128 configured to display, for example, a view of the surgical site inside a patient. As shown in the exemplary user console 120, user 107 located in seat 122 and viewing user display 128 may manipulate pedals 124 and/or handheld UIDs 126 to remotely command robotic arms 112 and/or surgical tools 104 mounted on the distal ends of robotic arms 112.

In some variations, bedside operator 106 may also operate the surgical robotic system 100 in an "over the bed" mode, in which the user is at a side of patient 102 and simultaneously manipulating a robotically-driven tool/end effector attached thereto, e.g., with a UID 126 held in one hand, and a manual laparoscopic tool. For example, the bedside operator's left hand may be manipulating a handheld UID 126 to command a surgical robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an exemplary procedure or surgery, patient 102 is prepped and draped in a sterile fashion to achieve anesthesia. Initial access to the surgical site may be performed manually with the surgical robotic system 100 in a stowed configuration or withdrawn configuration to facilitate access to the surgical site. Once access is completed, initial positioning and/or preparation of the surgical robotic system may be performed. During the procedure, user 107 in user console 120 may utilize pedals 124 and/or UID 122 to manipulate various end effectors and/or imaging systems to perform the surgery. Manual assistance may also be provided at the procedure table by sterile-gowned bedside personnel, e.g., bedside operator 106, who may perform tasks including but not limited to, retracting tissues or performing manual repositioning or tool exchange involving one or more robotic arms 112. Non-sterile personnel may also be present to assist user 107 at user console 120. When the procedure or surgery is completed, surgical robotic system 100 and/or user console 120 may be configured or set in a state to facilitate one or more post-operative procedures, including but not limited to cleaning and/or sterilization, and/or healthcare record entry or printout, whether electronic or hard copy, such as via user console 120.

In an embodiment, user 107 holds and moves UID 126 to provide an input command to move one or more actuators 114 of surgical robotic system 100. UID 126 may be communicatively coupled to surgical robotic system 100, e.g., via console computer system 110. UID 126 can generate spatial state signals corresponding to movement of UID 126, and the spatial state signals may be input to control motions of actuators 114 of surgical robotic system 100. Surgical robotic system 100 may use the control signals to control proportional motions of actuators 114. For example, a console processor of console computer system 110 can receive the spatial state signals and generate corresponding robot control signals that are output to robotic arms 112. Actuators 114 may be coupled to a corresponding surgical tool 104, and thus, the corresponding surgical tool 104 may be moved by the corresponding actuators 114 based on the robot control signals to mimic movement of UID 126. Similarly, interaction between user 107 and UID 126 can generate a grip signal to cause a jaw of a grasper of surgical tool 104 to close and grip tissue of patient 102.

In some aspects, communication between surgical platform 111 and the user console 120 may be through control tower 130, which may translate user commands from user console 120 to robotic control commands and transmit the converted commands to surgical platform 111. Control tower 130 may also transmit status and feedback from surgical platform 111 back to user console 120. The connections between surgical platform 111, user console 120, and control tower 130 may be via wired and/or wireless connections, and may be proprietary and/or performed using any of a variety of data communication protocols. Any wired connections may be optionally built into the floor and/or walls or ceiling of the operating room. Surgical robotic system 100 may provide video output to one or more displays, including displays within the operating room as well as remote displays accessible via the Internet or other networks. The video output or feed may also be encrypted to ensure privacy and all or portions of the video output may be saved to a server or electronic healthcare record system.

In an embodiment, processors of surgical robotic system, e.g., a console processor (FIG. 9) of user console 120, can receive user inputs and generate corresponding console configurations to drive one or more actuators of user console 120. The actuators of user console 120 can be associated with each of seat 122, display 128, or pedals 124 of surgical robotic system 100. For example, user console 120 can include one or more actuators 132 mechanically connected to seat 122 to cause horizontal translation, tilting, vertical movement, etc., of one or more components of seat 122. Similarly, display actuators can cause movement of display 128, and pedal actuators can cause movement of pedals 124. The actuator-caused movements of seat 122, display 128, and pedals 124 are described further below.

It will be appreciated that the operating room scene in FIG. 1 is illustrative and may not accurately represent certain medical practices.

Figure 2:
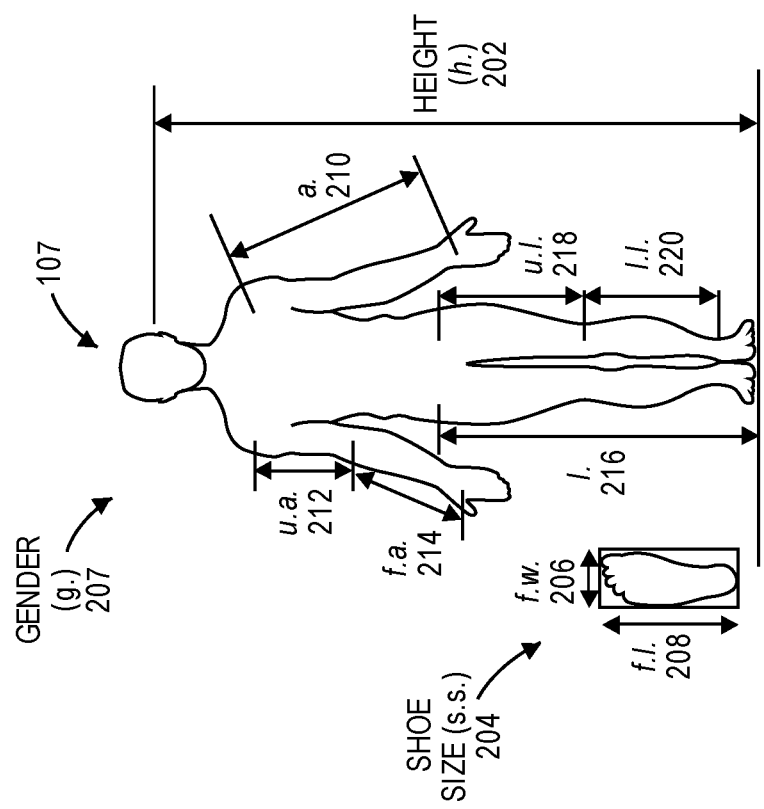
FIG. 2 is a schematic view of physical attributes of a user, in accordance with an embodiment.

Referring to FIG. 2, a schematic view of physical attributes of a user is shown in accordance with an embodiment. Surgical robotic system 100 may be shared by several users. For example, surgical robotic system 100 may be used by several surgeons at a hospital to perform different surgeries. The physical attributes of each user include numerous anatomical metrics. For example, each user is likely to have different physical characteristics and different ranges of motion. Likewise, each user is likely to have a different optimal initial console configuration of the system components, e.g., seat 122, display 128, and pedals 124. Accordingly, the capability to predict and automatically adjust the system components to accommodate the individual characteristics of each user provides value and mitigates the need for each user to separately adjust the system components when beginning a new surgery.

A processor of surgical robotic system 100, e.g., console processor, can receive one or more anthropometric inputs (or parameters). The anthropometric inputs include the user-specific anthropometric data, i.e., data corresponding to one or more physical attributes of user 107. It is contemplated that any physical attributes of user 107 may be input to the processor to generate initial console configurations as described below. Several physical attributes of user 107, however, are shown in FIG. 2 as examples of anthropometric characteristics associated with an optimal position of seat 122, display 128, or pedals 124 for a given user.

Primary physical attributes indicative of a preferred system configuration include: a height (h.) 202 of user 107 measured from the ground to eye level; and a shoe size (s.s.) 204 of user 107. Anthropometric input data corresponding to shoe size 204 can be a number and/or letter corresponding to any shoe-size system, e.g., size "11." Alternatively, anthropometric input data may be derived from such information. For example, user 107 may enter a shoe size 204, and the processor of surgical robotic system 100 may derive other physical characteristics, such as a foot width (f.w.) 206 or a foot length (f.l.) 208 from the information. A gender (g.) 207 of user 107 has also been shown to relate closely with certain system configuration settings. Accordingly, in an embodiment, user 107 may enter information about personal physical attributes into console computer system 110 at the beginning of a surgery, and at a minimum, the information may include height 202, shoe size 204, and (optionally) gender 207 of user 107.

Secondary physical attributes indicative of the preferred system configuration for user 107 include: arm length (a.) 210, which may be further broken down into upper arm length (u.a.) 212 measured from the shoulder to the elbow, and forearm length (f.a.) 214 measured from the elbow to the wrist; and leg length (l.) 216, which may be further broken down into upper leg length (u.l.) 218 measured from the hip to the knee, and lower leg length (l.l.) 220 measured from the knee to the ankle. The secondary physical attributes may be independent of, but related to, the primary physical attributes. For example, height 202 of user 107 may correlate to leg length 216 of user 107.

It would be cumbersome to measure all of the above-mentioned anatomical metrics to fully characterize the physique of user 107. Furthermore, user 107 may not know all of these physical attributes. For example, user 107 may not know his arm length 210, lower leg length 216, etc. In an embodiment, surgical robotic system 100 can predict the optimal initial console configuration of the console components based on a subset, e.g., two or more, of the above-mentioned anatomical metrics. For example, surgical robotic system 100 can predict the optimal initial console configuration based on an input of only height 202 and shoe size 204, and optionally gender 207 of user 107.

Figure 3:
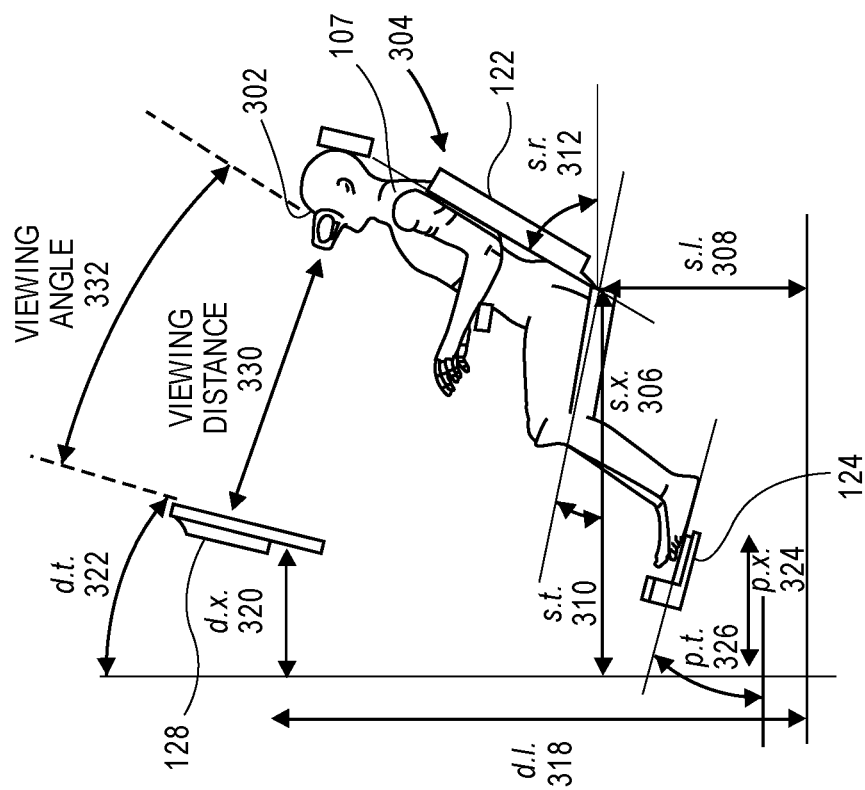
FIG. 3 is a schematic view of a user in a seated pose at a user console of a surgical robotic system, in accordance with an embodiment.

Referring to FIG. 3, a schematic view of a user 107 seated at user console 120 of a surgical robotic system 100 is shown in accordance with an embodiment. Like the physical attributes of user 107, the degrees of freedom defining the configuration of console components may be several. For example, the console configuration may depend on numerous configuration parameters, as shown in FIG. 3. In an embodiment, console actuators, e.g., seat actuators 132, adjust respective components, e.g., seat 122, of user console 120 to an initial console configuration 304. Initial console configuration 304 may be defined by the configuration parameters that establish a predicted optimal relative position between user 107 and the console components. For example, initial console configuration 304 of seat 122 can establish a predicted optimal relative position between a face 302 of user 107 and display 128 of surgical robotic system 100. The predicted optimal relative position can also be achieved by moving display 128 to the initial console configuration 304 using a display actuator. Likewise, pedals 124 may be moved into initial console configuration 304 by corresponding pedal actuators. Accordingly, initial console configuration 304 may be defined by one or more of a predicted optimal spatial position or orientation of seat 122, display 128, or pedals 124.

In an embodiment, the configuration parameters defining the spatial position or orientation of seat 122 include a seat translation (s.x.) parameter 306 and a seat lift (s.l.) parameter 308. Seat translation parameter 306 can be a distance measured horizontally from seat 122 to a datum associated with a frame of user console 120. For example, seat translation parameter 306 may be the distance between seat 122 and a column supporting display 128 in front of seat 122. Seat lift parameter 308 can be a distance measured vertically from seat 122 to a datum associated with the frame of user console 120. For example, seat lift parameter 308 may be the distance between seat 122 and a floor that supports seat 122. The spatial position or orientation of seat 122 can also be defined by a seat tilt (s.t.) parameter 310. Seat tilt parameter 310 may be an angle between a horizontal plane and a plane extending parallel to an upper surface of seat 122 on which user 107 sits. The spatial position or orientation of seat 122 can also be defined by a seat recline (s.r.) parameter 312. Seat recline parameter 312 may be an angle between the horizontal plane and a back of seat 122 against which user 107 leans. Other parameters that define the spatial position or orientation of seat 122, which are omitted here for brevity, include a translation, lift, or tilt parameter for a headrest of seat 122, an armrest of seat 122, a lumbar support of seat 122, etc.

A spatial position or orientation of display 128 can be defined by similar configuration parameters, including a display lift (d.l.) parameter 318, a display translation (d.x.) parameter 320 and a display tilt (d.t.) parameter 322. Display translation parameter 320 can be a distance measured horizontally from display 128 to a datum associated with a frame of user console 120. For example, display translation parameter 320 may be the distance between display 128 and a column supporting display 128 in front of display 128. Display tilt parameter 322 may be an angle between a horizontal plane and a plane extending parallel to a viewing plane of display 128.

A spatial position or orientation of pedals (or a panel of pedals) 124 can be defined by similar configuration parameters, including a pedal translation (p.x.) parameter 324 and a pedal tilt (p.t.) parameter 326. Pedal translation parameter 324 can be a distance measured horizontally from pedals 124 to a datum associated with a frame of user console 120. For example, pedal translation parameter 324 may be the distance between pedals 124 and a column supporting display 128 in front of pedals 124. Pedal tilt parameter 326 may be an angle between a horizontal plane and a plane extending parallel to a surface of pedals 124 on which a foot of the user rests.

The configuration parameters defined above determine the spatial position or orientation of user 107 when the user is seated at user console 120. Accordingly, the configuration parameters define a relative position between user 107 and components of user console 210. For example, the relative position may be a viewing distance 330 measured between face 302 of user 107 and display 128. Similarly, the relative position may be a viewing angle 332 measured between a plane extending along the viewing plane of display 128 and a plane that is normal to a line of sight of user 107. Viewing angle 332 can be described as a relative tilt between display 128 and face 302. The relative position of user 107 impacts a comfort of user 107 during the surgery. For example, viewing distance 330 and viewing angle 332 can affect an ability of user 107 to view the display screen correctly and comfortably.

In an embodiment, user console 120 establishes as an output the optimal relative position of user 107 based on input physical parameters of user 107. That is, user 107 can enter information related to the physical attributes described above, and the processor will predict the optimal relative position of user 107, and set the configuration parameters to cause the console actuators to move the console components such that user 107 is moved into the optimal relative position. Prediction of the configuration parameter outputs based on the input physical parameters may be made using machine learning. A method of predicting and adjusting console components (seat 122 is provided by way of example) of surgical robotic system 100 to the optimal initial console configuration 304 is described below.

Figure 4A:
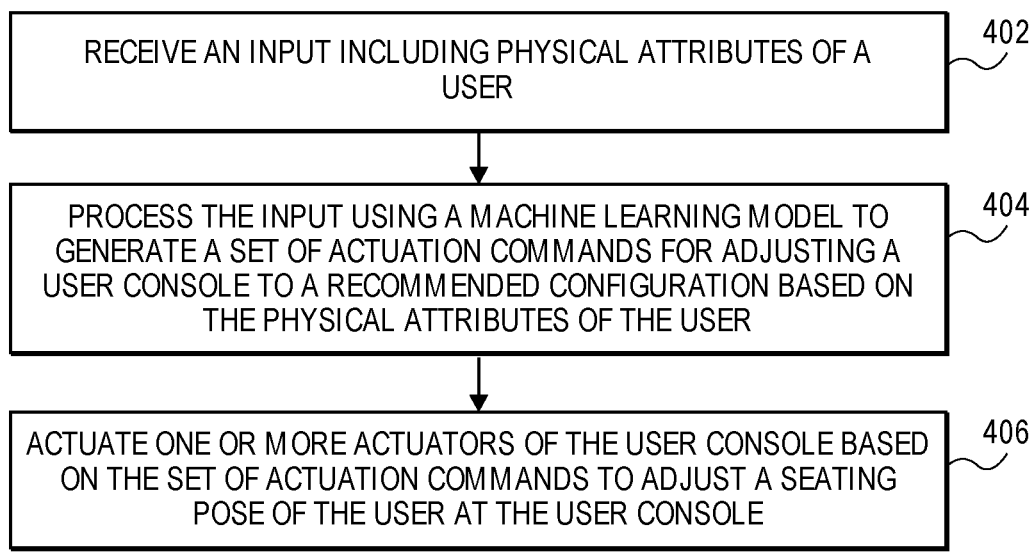
FIGS. 4A-4B are flowcharts of methods of adjusting configurations of a user console of a surgical robotic system, in accordance with an embodiment.
Figure 4B:
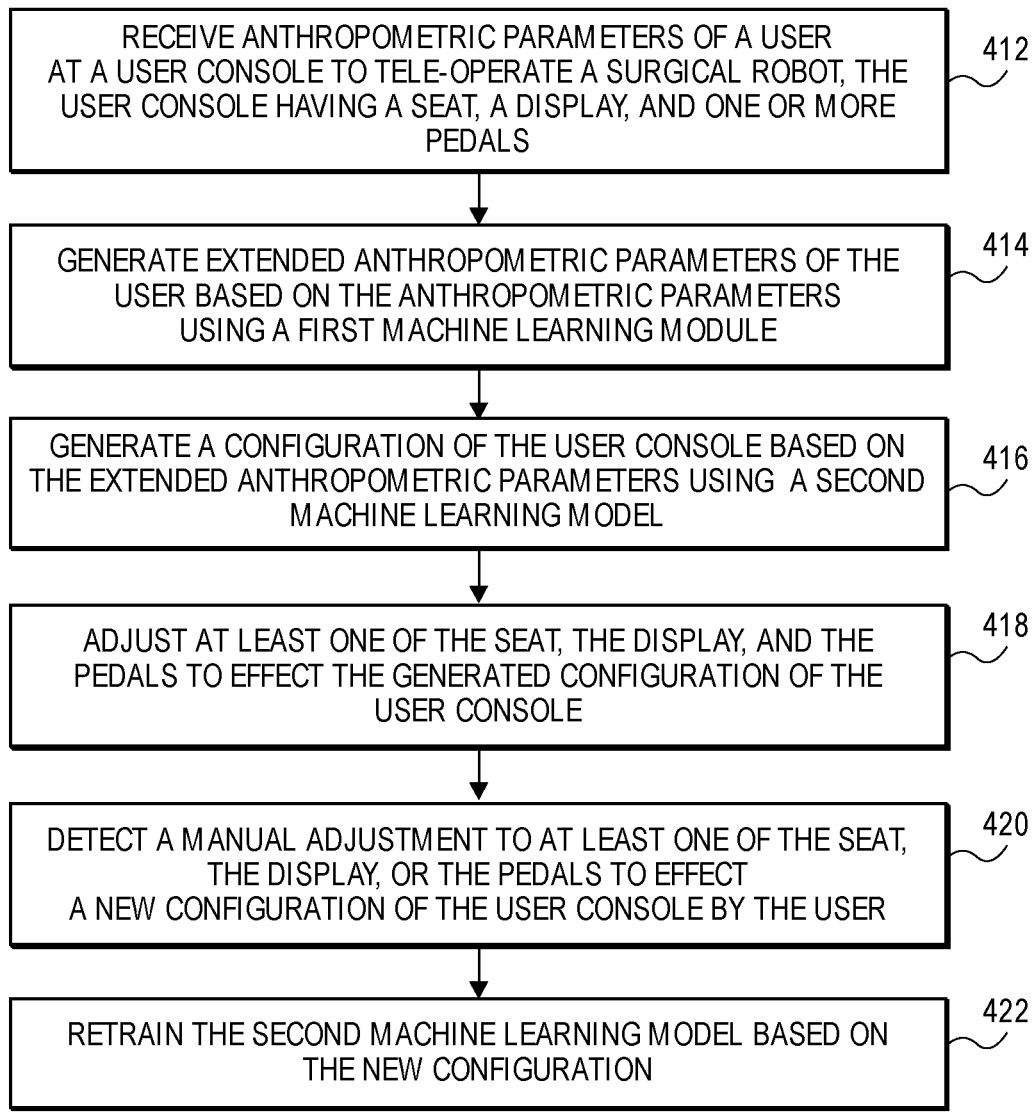

Referring to FIGS. 4A-4B, flowcharts of a method of adjusting configurations of a user console of a surgical robotic system are shown in accordance with an embodiment. For example, seat 122 and/or other console components of a surgical robotic system 100 can be adjusted to an initial console configuration 304. Operations of the methods illustrated in FIGS. 4A-4B correspond to the illustrations of FIGS. 5-7, and thus, FIGS. 4A-7 are described in combination below.

Figure 5:
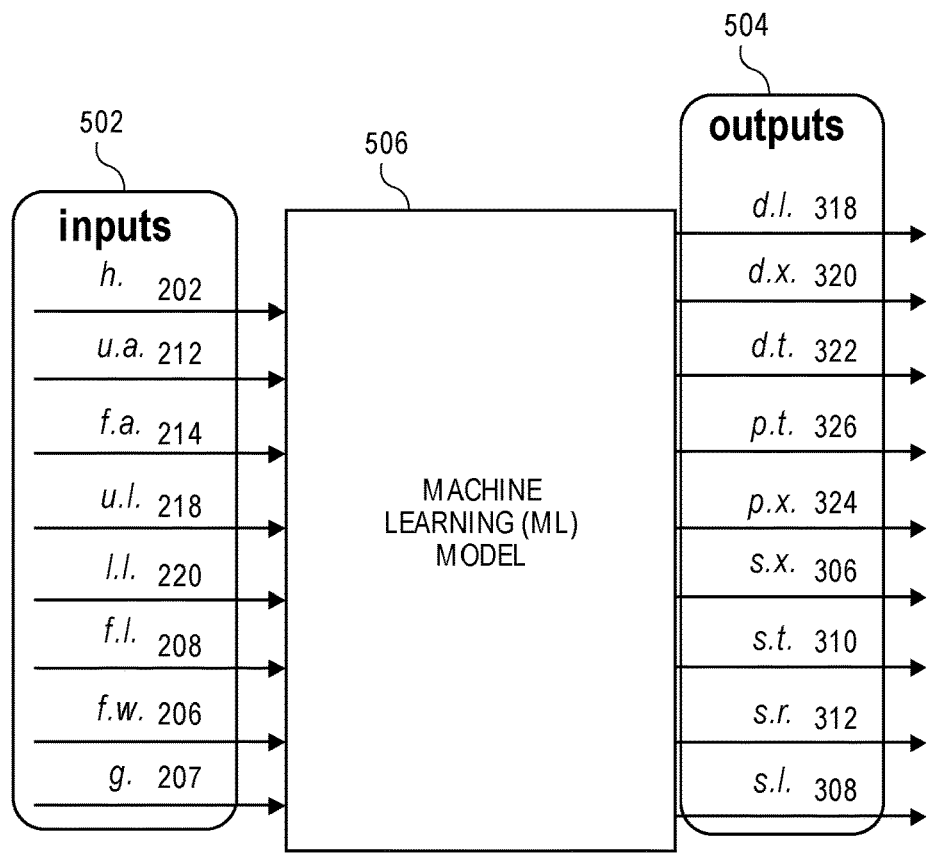
FIG. 5 is a block diagram of a single-stage machine learning model, in accordance with an embodiment.

Referring to FIG. 5, a block diagram of a single-stage ML model 506 is shown in accordance with an embodiment. The block diagram of FIG. 5 is described here in combination with the method of FIG. 4A. At operation 402, a processor of surgical robotic system 100 can receive one or more anthropometric inputs 502 corresponding to one or more physical attributes of user 107. Anthropometric inputs 502 received or derived by the processor can include physical characteristics of user 107 seated at user console 120 to tele-operate a surgical robot, including: height 202, gender 207, upper arm length 212, forearm length 214, upper leg length 218, lower leg length 220, foot length 208, or foot width 206 of user 107. Anthropometric inputs 502 can represent data entered manually by user 107 using input devices such as a graphical user interface, a keyboard, and/or a mouse, etc. In an embodiment, user console 120 is equipped with a vision system configured to detect and/or measure certain physical attributes of user 107. For example, a camera of the vision system may capture an image of the user 107 and compare the image to reference data in order to determine height 202 or shoe size 204 of user 107. Alternatively, user 107 may enter a unique identifier, e.g., an employee identification number, and the processor may retrieve previously stored physical attributes data from a database entry corresponding to user 107.

At operation 404, the processor of surgical robotic system 100 processes the inputs 502 using an ML model 506 to generate a set of actuation commands for adjusting user console 120. The actuation commands can include console configuration parameters 504 corresponding to an optimized (or recommended) initial console configuration based on anthropometric metrics of the user. More particularly, the set of actuation commands can be used to adjust user console 120 to the recommended configuration based on the physical attributes of user 107.

In an embodiment, the recommended configuration effects a seating pose of user 107, e.g., a pose of seat 122, at user console 120. The outputs 504 can include one or more of: display lift parameter 318, display translation parameter 320, display tilt parameter 322, pedal tilt parameter 326, pedal translation parameter 324, seat translation parameter 306, seat recline parameter 312, seat lift parameter 308, or seat tilt parameter 310, which may be used by the processor to actuate one or more actuators of user console 120 to adjust the positions and angles of seat 122, display 128, and/or pedals 124. Accordingly, seating pose is represented by one or more parameters including seat translation parameter 306, seat lift parameter 308, seat tilt parameter 310, or seat recline parameter 312. Adjustment of the seating pose based on the outputs 504 can effect a relative viewing distance and angle between user 107 and display 128.

To generate the set of actuation commands, the processor can process the anthropometric inputs 502 using a machine learning algorithm. The ML models described with respect to FIGS. 5-6 can be regression models that are trained to correlate an input to an output.

In some implementations, the ML model (506 or 606) may be trained by data collected from hundreds of surgeons and volunteers, whose anthropometric metrics, such as height, upper and forearm lengths, upper and lower leg lengths, and/or foot length, have been measured. The accumulated anthropometric data can be correlated to an output, such as console configuration parameters. For example, the surgeons and volunteers that are measured to accumulate the anthropometric data may be asked to adjust the user console to the best of their abilities. The adjustments made by the users represent user preferences, which can be related to the measured anthropometric data for the users. Accordingly, user preferences in the console setting, such as seat, display and pedal placement for various seat poses, have been collected as "ground truth" for the machine training purpose. In some implementations, ML model 506 (or 606) can include a regularized regression model. For example, a regularized multivariable regression algorithm can be applied to model the correlations between the user preferences in console settings and the physical attributes of the users. After training the ML model, the regularized regression model can recommend a configuration of user console 120 based on a correlation between the physical attributes of a user and the user preferences in user console configurations. More user preference data can be collected to test and fine tune the regression model. The ML model proves to be a reliable predictor for optimum initial console settings, and recommended initial console settings may save precious time for surgeons in operating rooms.

Figure 6:
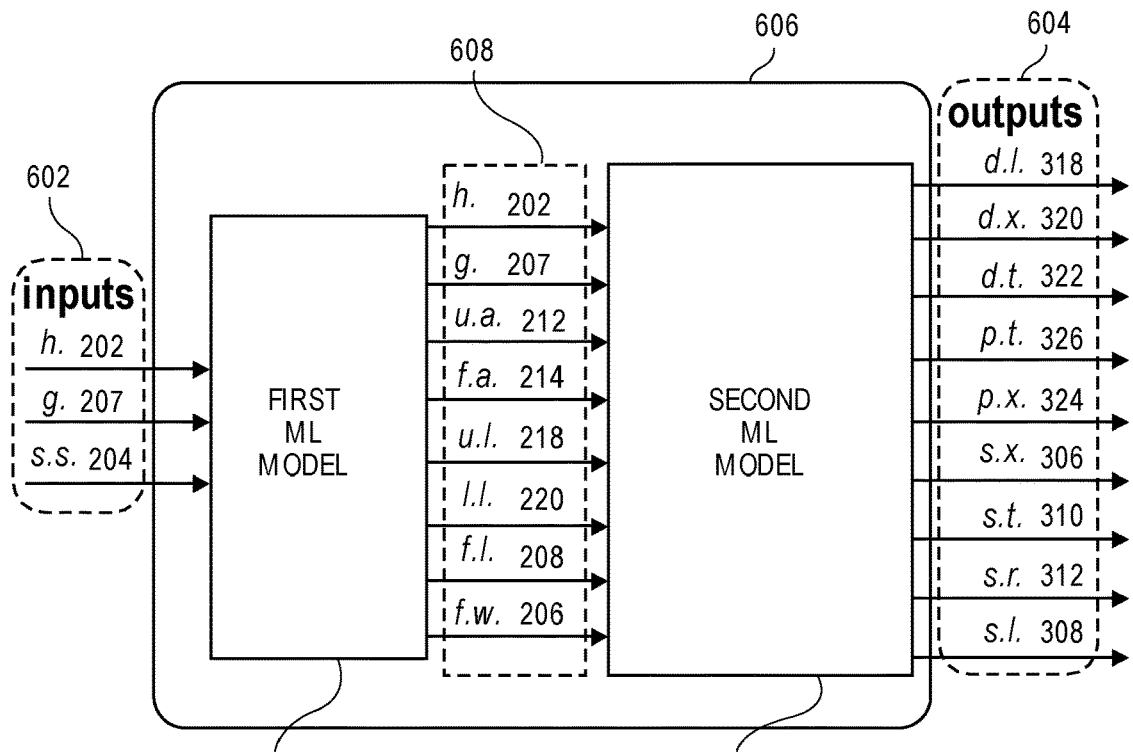
FIG. 6 is a block diagram of a multi-stage machine learning model, in accordance with an embodiment.

In some implementations, the accumulated anthropometric data can be correlated to additional anthropometric data (see extended anthropometric parameters of FIG. 6). Training data can be obtained from measurements of users, as described above, or from published sources of anthropometric data. The accumulated anthropometric data can be used to correlate an input set of anthropometric parameters to an output set of anthropometric parameters. For example, a regularized multivariable regression algorithm can be applied to model correlations between an output set of parameters including one or more of upper arm length 212, forearm length 214, upper leg length 218, lower leg length 220, foot length 208, or foot width 206, to an input set of parameters including one or more of height 202, gender 207, or shoe size 204 (see FIG. 6).

At operation 406, one or more actuators of user console 120 can be actuated based on the set of actuation commands. For example, actuators connected to seat 122, display 128, and/or pedals 124 can be controlled according to the generated configuration of user console 120 to adjust a pose of seat 122, display 128, or pedals 124, a position or angle of seat 122, display 128, or pedals 124, or a position of seat 122, display 128, or pedals 124 relative to each other or other components of user console 120. Seat and display adjustment can include adjusting one or more configuration parameters, including: seat translation 306, seat lift 308, seat tilt 310, seat recline 312, display translation 320, display lift 318, or display tilt 322. Accordingly, the configuration of user console 120 can be adjusted.

FIG. 5 illustrates a single-stage regression model that relates the console configuration parameters to a set of physical attributes, which include physical attributes that are not readily known or convenient to measure. For example, user 107 may not know his upper leg length 218, and thus, may be unable to enter every input required to generate the initial console configuration. As described below, in an embodiment, user 107 is allowed to enter information that is readily known, and ML model 506 can derive information that is not readily known as inputs to a predictive model used to generate console configuration parameters 504.

Referring to FIG. 6, a block diagram of a multi-stage ML model 606 is shown in accordance with an embodiment. The block diagram of FIG. 6 is described here in combination with the method of FIG. 4B. At operation 412, one or more anthropometric parameters 602 of user 107 are received.

In an embodiment, ML model 606 used to predict console configuration parameters 604 (similar to outputs 504) based on anthropometric inputs 602 (similar to inputs 502) can include at least two stages. The multi-stage ML model 606 can include a first ML model 614 to receive anthropometric inputs 602, and a second ML model 616 to output recommended configurations 604. The ML models 614 and 616 may be arranged in a serial order. For example, first ML model 614 may output a set of extended anthropometric parameters 608 of the user based on inputs 602. The set of extended anthropometric parameters 608 may be fed directly to second ML model 616 to generate outputs 604. Each ML model 614, 616 can include respective regularized linear or nonlinear regression ML models designed to estimate or predict an output based on an input.

At operation 414, extended anthropometric parameters 608 of user 107 are generated based on the received anthropometric parameters 602. In an embodiment, first ML model 614 correlates a smaller set of readily known physical attributes to a larger set of physical attributes. For example, there are more anthropometric parameters 608 output by first ML model 614 than anthropometric inputs 602. By way of example, anthropometric inputs 602 may be the primary physical attributes described above, such as two or more of height 202, shoe size 204, or gender 207 of user 107. Such information is generally readily known by users. Accordingly, user 107 can enter the information and the anthropometric parameters can be received from the user for processing. In an embodiment, the anthropometric inputs 602 entered into first ML model 614 include just height 202 and shoe size 204 of user 107. Anthropometric inputs 602 can therefore be a subset of inputs 502 used in a single-stage ML model.

First ML model 614 may include a predictive regression model simulating a correlation between the readily known anthropometric parameters 602 and the extended anthropometric parameters 608. Extended anthropometric parameters 608 output by first ML model 614 may include the anthropometric inputs 602 and one or more additional physical attributes or metrics that correlate to the entered data. The additional physical attributes can be any of the secondary physical attributes described above. For example, in addition to height 202, and/or gender 207, extended anthropometric parameters 608 can include upper arm length 212, forearm length 214, upper leg length 218, lower leg length 220, foot length 208, or foot width 206 (foot metrics, for example, may be derived from shoe size 204). Training and testing data for the first ML model 614 may come from measurements of surgeons and volunteers, as well as from open anthropometric datasets, e.g., datasets published on the Internet.

At operation 416, second ML model 616 is used to generate a configuration of user console 120 based on extended anthropometric parameters 608. Second ML model 616 can include a predictive regression model simulating a correlation between extended anthropometric parameters of users and their preferences in user console configurations. For example, the predictive regression model can simulate a correlation between extended anthropometric parameters 608 of user 107 and the preferred user console configuration of user 107.

In an embodiment, second ML model 616 correlates extended anthropometric parameters 608 to console configuration parameters 604. Second ML model 616 may be similar to the single-stage ML model 506 illustrated in FIG. 5. More particularly, second ML model 616 can be trained to predict optimal configuration parameters 604, e.g., a display lift parameter 318, display translation parameter 320, display tilt parameter 322, pedal tilt parameter 326, pedal translation parameter 324, seat translation parameter 306, seat recline parameter 312, or seat lift parameter 308, based on the extended set of anthropometric inputs 608, e.g., height 202, gender 207, upper arm length 212, forearm length 214, upper leg length 218, lower leg length 220, foot length 208, or foot width 206 of user 107. As similarly described above with respect to operation 404 of FIG. 4A, the recommended configuration of user console 120 includes a seating pose of user 107, e.g., a pose of seat 122 and/or other components of user console 120. For example, the configuration can include positions and angles of seat 122, display 128, and/or pedals 124.

As similarly described above with respect to operation 406 of FIG. 4A, at operation 418 of FIG. 4B one or more actuators of user console 120 can be actuated based on parameters 604 to adjust at least one of seat 122, display 128, and/or pedals 122 to effect the generated recommended configuration of user console 120. For example, actuators connected to seat 122, display 128, and/or pedals 122 can be controlled to adjust the user console components to the recommended configuration.

Figure 7:
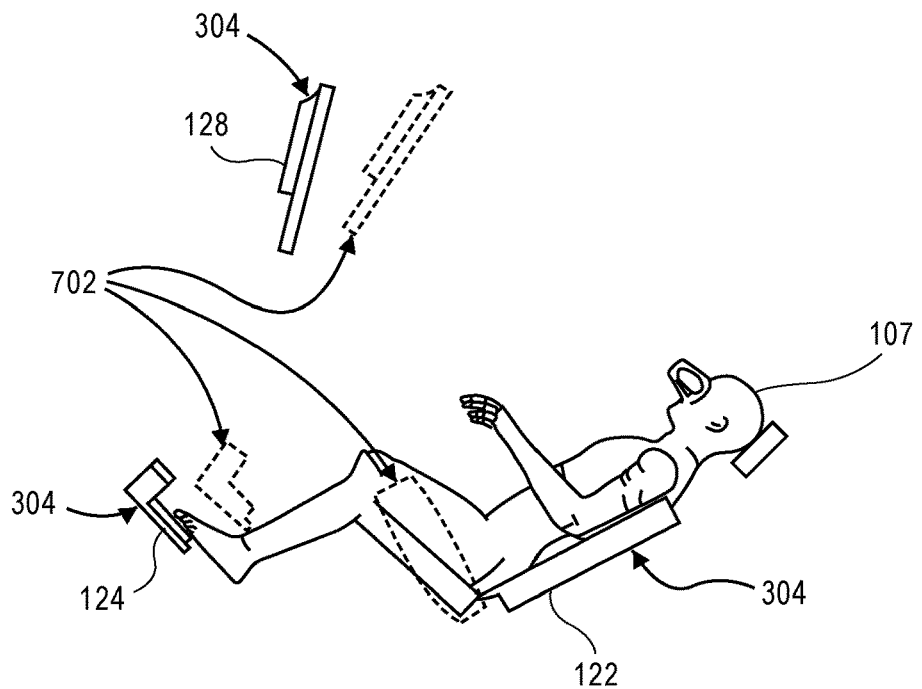
FIG. 7 is a schematic view of a user in a reclined pose at a user console of a surgical robotic system, in accordance with an embodiment.

Referring to FIG. 7, a schematic view of a user 107 in a reclined pose at the user console of the surgical robotic system is shown in accordance with an embodiment. At operation 406 of FIG. 4A, or operation 418 of FIG. 4B, seat 122 (and/or other console components) is adjusted to initial console configuration 304 that is predicted to be an optimal starting position for user 107. Seat actuators 132 can be coupled to the processor, and the processor may transmit the set of console configuration parameters 504 (or 604) generated by ML model 506 (or 606) to drive seat actuators 132. In response to receiving the set of parameters 504 (or 604) from processor, console actuators can automatically adjust user console 120 to an initial console configuration 304, which is defined by the configuration parameters of actuation output signals 504 (or 604).

Initial console configuration 304 establishes the relative position between user 107 and surgical robotic system 100. For example, the relative position may include a relative orientation of face 302 of user 107 and display 128 of surgical robotic system 100. That relative orientation can include an initial viewing distance 330 or viewing angle 332, as described above. Initial console configuration 304 is a predicted optimal starting position for user 107 based on the modeled anthropometric data. The ML model may be trained using data collected from a substantial population, and thus, the predicted optimal starting position may be an ideal long-term position for user 107. The ML model, however, may not take into account every physical attribute of user 107, and thus, user 107 may want to adjust a component of surgical robotic system 100 after user console 120 has been moved into initial console configuration 304.

Adjustments to the console configuration and retraining of ML model based on such adjustments are described below with reference to FIG. 4B. It will be appreciated, however, that such operations may be appended to the method of FIG. 4A. At operation 420, the processor of surgical robotic system 100 detects a manual adjustment to at least one of seat 122, display 128, or pedals 124 of user console 120. The manual adjustment can be made by user 107 to effect a new configuration, different than the recommended configuration generated by the ML learning model(s). For example, the manual adjustment may be of seat 122 to an adjusted position 702 from initial console configuration 304. User 107 may prefer a different console configuration to the initial console configuration 304. User 107 may want to tilt display 128, raise pedals 124, or tilt seat 122. For example, user 107 may manually adjust seat tilt parameter 310 to a position that the user finds more comfortable. Similarly, user 107 can adjust display tilt parameter 322 or pedal translation parameter 324 to a more comfortable position.

At operation 422, the processor of surgical robotic system 100 may retrain one or more of the ML learning models that generated the recommended configuration. For example, in a single-stage model, ML learning model 506 may be retrained. In a multi-stage model, second ML model 616 may be retrained. The retraining may be based on the new configuration that user 107 adjusted user console 120 to. Retraining the ML models, e.g., second ML model 616, may occur automatically in response to detecting the manual adjustment made by user 107 to the console configuration. Alternatively, the configuration parameters defining adjusted position 702 can be saved, e.g., stored in a memory of user console 120, for future access. More particularly, information about manual adjustments made by one or more users after configuring console in the recommended initial configuration can be used to enrich the training data, which may cause an update to the recommended console configuration parameters 504 based on the same anthropometric inputs 502. The enriched training data can relate a specific set of inputs 502 (or 602) to a specific user preference that is different than a predicted user preference, and accordingly, the updated ML model may generate a different set of configuration parameters based on anthropometric inputs 502, which improve the prediction. On the other hand, the adjustment may not be to every parameter, and accordingly, the updated ML model may generate the same configuration parameters for at least some of the parameters, which reinforces the prediction in some aspects.

Figure 8:
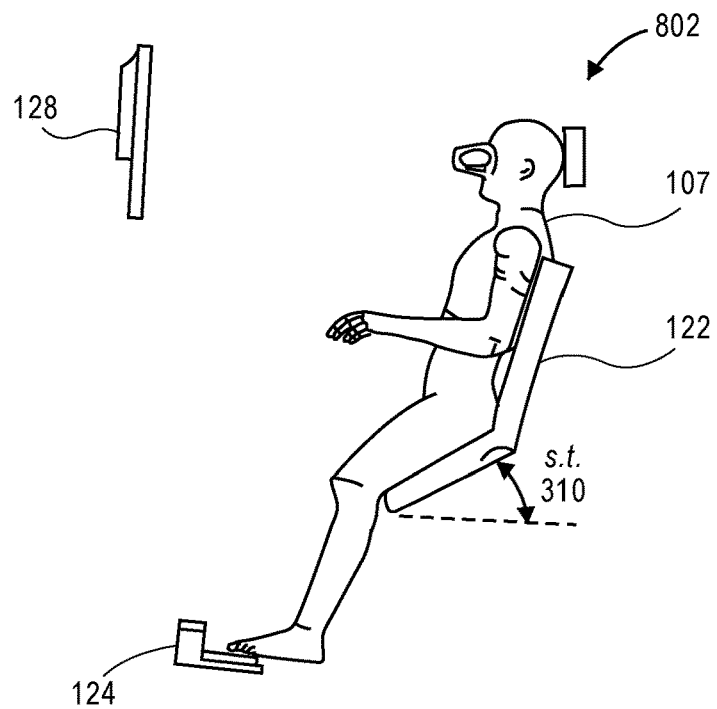
FIG. 8 is a schematic view of a user in a standing pose at a user console of a surgical robotic system, in accordance with an embodiment.

Referring to FIG. 8, a schematic view of the user 107 in a standing pose 802 at the user console of the surgical robotic system is shown in accordance with an embodiment. User 107 can choose from various postural schemes within which respective initial console configurations 304 may be found. Surgical robotic system 100 may operate in one or more of a seated mode, a reclined mode, or an elevated mode. For example, the pose of seat 122 can include one of an elevated pose, a seated pose, or a reclined pose. An example of surgical robotic system 100 operating in the seated mode is illustrated in FIG. 3. In the seated mode, user 107 is supported by seat 122 in a sitting position in which the thighs of user 107 are generally parallel to the ground and the back of user 107 is upright. An example of surgical robotic system 100 operating in the reclined mode is illustrated in FIG. 7. In the reclined mode, user 107 is supported by seat 122 in a reclined position in which a medial axis of user 107 is tilted toward the ground. An example of surgical robotic system 100 operating in the elevated mode is illustrated in FIG. 8. In the elevated mode, the user 107 is supported by the seat 122 in a standing position 802 in which user 107 bears weight on his feet. Standing position 802 can be further characterized by the sitting surface of seat 122 having seat tilt parameter 310 at an angle that causes the sitting surface to face in a forward direction, e.g., toward display 128.

Figure 9:
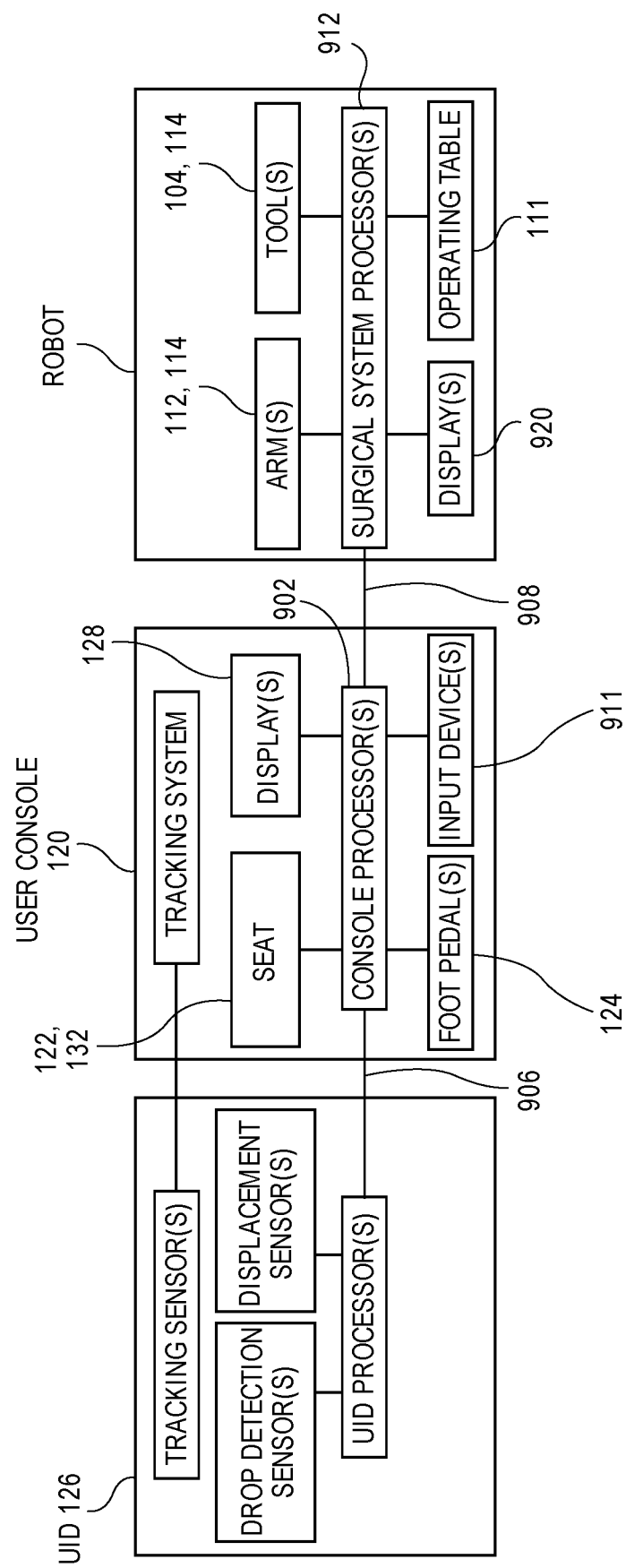
FIG. 9 is a block diagram of a surgical robotic system, in accordance with an embodiment.

Referring to FIG. 9, a block diagram of a computer portion of a surgical robotic system is shown in accordance with an embodiment. Surgical robotic system 100 can include UID(s) 126, user console 120 having computer system 110, and a robot including robotic components 104, 112. Computer system 110 and UID 126 have circuitry suited to specific functionality, and thus, the diagrammed circuitry is provided by way of example and not limitation.

One or more processors of user console 120 can control portions of surgical robotic system 100, e.g., surgical robotic arms 112 and/or surgical tools 104. UID 126 may be communicatively coupled to computer system 110 and/or surgical robotic system 100 to provide input commands that are processed by one or more processors of system 100 to control movement of surgical robotic arm 112 and/or surgical tool 104 mounted on the arm. For example, UID 126 may communicate electrical command signals 906, e.g., spatial state signals generated by one or more UID processor(s) in response to signals from tracking sensor(s). Spatial state signals may also be generated by one or more displacement sensors connected to the UID processor(s), and the UID processor(s) can electrically communicate with other input sensors such as drop detection sensors that generate control signals when the UID 126 is dropped. The electrical signals output by the UID processor(s) in response to the sensor tracking signals may be input to cause (or pause) motion of surgical robotic system 100.

The input electrical signals 906 may be transmitted by the UID processor(s) to one or more console processors 902 of computer system 110 via a wired or wireless connection. For example, UID 126 may transmit the command signals 906 to console processor(s) 902 via electrical wire. Alternatively, UID 126 may transmit command signals 906 to console processor(s) 902 via a wireless communication link. The wireless communication link may be established by respective RF circuitry of user console 120 and UID 126. The wireless communication can be via radiofrequency signals, e.g., Wi-Fi or short range signals and/or suitable wireless communication protocols such as Bluetooth.

Console processor(s) 902 of computer system 110 may execute instructions to carry out the different functions and capabilities described above. Instructions executed by console processor(s) 902 of user console 120 may be retrieved from a local memory (not shown), which may include a non-transitory machine-readable medium. The instructions may be in the form of an operating system program having device drivers to control components of user console 120, e.g., seat actuator(s) 132 coupled to seat 122.

In an embodiment, console processor 902 controls components of user console 120. For example, one or more seat actuators 132 can receive commands from console processor(s) 902 to control movement of seat 122. Commands from console processor(s) 902 may also control movement of display 128 or pedals 124 via corresponding actuators. The controlled actuators, e.g., seat actuator(s) 132, can move respective components, e.g., seat 122, in one or more degrees of freedom, such as forward/backward translation, tilt, vertical position, etc. Console processor 902 can also transmit video data for presentation on display 128. Accordingly, console processor(s) 902 can control operation of user console 120. Input commands to seat actuator(s) 132 or console processor 902 can be entered by the user via foot pedals 124 or another input device 911 such as a keyboard or a joystick.

User console 120 can control the console components to establish initial console configuration 304 as described above. User 107 can enter anthropometric inputs 502 (or 602) into the computer system using one or more input device 911, such as a keyboard, and/or a graphical user interface presented by display 128. Console processor 902 can generate console configuration parameters 504 (or 604) based on the inputs using ML model 506 (or 606), and drive console actuators (e.g., seat actuators 132) to adjust one or more of seat 122, display 128, or pedals 124 into the optimal initial configuration 304.

Console processor 902 can output tracking signals 908 to other components of surgical robotic system 100 via a link.

Tracking signals 908 may be transmitted and used to control movement of a robot of surgical robotic system 100. In an embodiment, user console 120 is communicatively coupled to downstream components of surgical robotic system 100, e.g., control tower 130, via wired or wireless links. The links can transmit tracking signals 908 to one or more surgical system processor(s) 912. For example, at least one processor 912 can be located in control tower 130, and may be communicatively coupled to system components, such as robotic arms 112, surgical tools 104, surgical robotic platform 111, or one or more displays 920. Actuators 114 of surgical robotic system 100 may receive control signals from surgical system processor(s) 912 to cause movement of arm 112 and/or tool 104 corresponding to tracking signals 908 based on movement of UID 126.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A user console system of a surgical robot, comprising:
    a processor configured to:
        process an input comprising one or more known anthropometric parameters of a user,
        generate an extended set of anthropometric parameters of the user based on the input using a first regression model, and
        generate an initial configuration of the user console based on the extended set of anthropometric parameters using a second regression model; and
    one or more actuators coupled to the processor, a seat, and a display, wherein the one or more actuators are configured to automatically actuate the user console to adjust the seat and the display to the initial configuration for the user.

2. The user console system of claim 1, further comprising one or more pedals.

3. The user console system of claim 2, wherein the initial configuration of the user console is represented by one or more parameters including a seat translation, a seat lift, a seat tilt, a seat recline, a display translation, a display lift, a display tilt, a pedal translation, or a pedal tilt.

4. The user console system of claim 1, wherein the one or more known anthropometric parameters include a gender or a shoe size of the user.

5. The user console system of claim 1, wherein the extended set of anthropometric parameters correspond to non-postural physical attributes of the user and include one or more of a height, a gender, an upper arm length, a forearm length, an upper leg length, a lower leg length, a foot width, or a foot length of the user.

6. The user console system of claim 1, wherein the first regression model simulates a correlation between the one or more known anthropometric parameters and the extended set of anthropometric parameters of users, and the second regression model simulates a correlation between the extended set of anthropometric parameters of users and their preferences in user console configurations.

7. A user console of a surgical robotic system, comprising:
    a seat;
    a display;
    one or more actuators coupled to the seat and the display; and
    a processor configured to:
        receive an input including a plurality of physical attributes of a user,
        process the input using a machine learning model to generate a set of actuation commands for adjusting the user console to a recommended configuration based on the plurality of physical attributes of the user, wherein the recommended configuration effects a seating pose of the user at the user console, and a relative viewing distance and angle between the user and the display, and
        actuate the one or more actuators of the user console based on the set of actuation commands to adjust the seat and the display.

8. The user console of claim 7, wherein the plurality of physical attributes a gender or a shoe size of the user.

9. The user console of claim 7, wherein the machine learning model includes a regularized regression model that recommends a configuration of the user console based on a correlation between the plurality of physical attributes of the user and user preferences in user console configurations.

10. The user console of claim 7, wherein adjusting the seat and the display comprises adjusting one or more parameters including a seat translation, a seat lift, a seat tilt, a seat recline, a display translation, a display lift, or a display tilt.

11. A method of adjusting configurations of a user console of a surgical robotic system, the method comprising:
    receiving one or more anthropometric parameters of a user to tele-operate a surgical robot at a user console, the user console having a seat, a display, and one or more pedals;
    generating, by a processor, a plurality of extended anthropometric parameters of the user based on the received anthropometric parameters using a first machine learning model;
    generating, by the processor, a configuration of the user console based on the plurality of extended anthropometric parameters using a second machine learning model, the configuration of the user console comprising a pose of the seat, and positions and angles of the display and the one or more pedals; and
    adjusting at least one of the seat, the display, or the one or more pedals to effect the generated configuration of the user console.

12. The method of claim 11, wherein the one or more anthropometric parameters are received from the user.

13. The method of claim 11, wherein the received anthropometric parameters comprise at least two of a height, a gender, or a shoe size that are readily known to the user.

14. The method of claim 13, wherein the plurality of extended anthropometric parameters include one or more of a height, a gender, an upper arm length, a forearm length, an upper leg length, a lower leg length, a foot width, or a foot length of the user.

15. The method of claim 14, wherein the first machine learning model comprises a predictive regression model simulating a correlation between the readily known anthropometric parameters and the plurality of extended anthropometric parameters.

16. The method of claim 11, wherein the second regression model comprises a predictive regression model simulating a correlation between the plurality of extended anthropometric parameters of the user and user preferences in user console configurations.

17. The method of claim 11, wherein the pose of the seat includes an elevated pose, a seated pose, or a reclined pose.

18. The method of claim 17, wherein the pose of the seat is represented by one or more parameters including a seat translation, a seat lift, a seat tilt, or a seat recline.

19. The method of claim 11, wherein adjusting the user console comprises actuating, by the processor, one or more actuators of the user console to adjust the pose of the seat, and the positions and angles of the display and the one or more pedals according to the generated configuration of the user console.

20. The method of claim 11, further comprising:
  detecting a manual adjustment to at least one of the seat, the display, or the one or more pedals of the user console to effect a new configuration by the user; and
  retraining, by the processor, the second machine learning model based on the new configuration.

* * * * *